United States Patent
Lange et al.

(10) Patent No.: US 10,035,783 B2
(45) Date of Patent: Jul. 31, 2018

(54) PROCESS FOR THE PRODUCTION OF 1,4-BUTANEDIOL AND TETRAHYDROFURAN FROM FURAN

(71) Applicant: SHELL OIL COMPANY, Houston, TX (US)

(72) Inventors: Jean Paul Andre Marie Joseph Ghislain Lange, Amsterdam (NL); Rene Johan Haan, Amsterdam (NL)

(73) Assignee: SHELL OIL COMPANY, Houston, TX (US)

( * ) Notice: Subject to any disclaimer, the term of this patent is extended or adjusted under 35 U.S.C. 154(b) by 0 days.

(21) Appl. No.: 15/564,494

(22) PCT Filed: Apr. 7, 2016

(86) PCT No.: PCT/EP2016/057577
§ 371 (c)(1),
(2) Date: Oct. 5, 2017

(87) PCT Pub. No.: WO2016/162397
PCT Pub. Date: Oct. 13, 2016

(65) Prior Publication Data
US 2018/0072692 A1    Mar. 15, 2018

(30) Foreign Application Priority Data
Apr. 9, 2015 (EP) .................... 15162903

(51) Int. Cl.
C07D 307/00 (2006.01)
C07D 307/08 (2006.01)
C07C 29/17 (2006.01)

(52) U.S. Cl.
CPC .......... C07D 307/08 (2013.01); C07C 29/172 (2013.01)

(58) Field of Classification Search
CPC ............................ C07D 307/08; C07C 29/172
USPC ....................................................... 549/429
See application file for complete search history.

(56) References Cited

U.S. PATENT DOCUMENTS 5,905,159 A    5/1999 Fischer et al.

FOREIGN PATENT DOCUMENTS

| CN | 107001203 A | 8/2017 |
| EP | 0061042 A1 | 9/1982 |
| EP | 3227267 A1 | 10/2017 |
| GB | 550105 A | 12/1942 |
| WO | 0222593 A1 | 3/2002 |
| WO | 2011002912 A2 | 1/2011 |
| WO | 2012041990 A1 | 4/2012 |

OTHER PUBLICATIONS

International Search Report and Written Opinion received for PCT Patent Application No. PCT/EP2016/057577, dated Jun. 27, 2016, 10 pages.
Shinozaki, "Catalytic hydrogenation of furan derivatives. 7. The vapor phase hydrogenation of furan with a nickel catalyst", Chemical Abstracts Service, retrieved from STN Database accession No. 1979:71978, Dec. 31, 1979, XP002744530.
Hoydonck et al., "Furfural and Derivatives", Ullmann's Encyclopedia of Industrial Chemistry, vol. 16, 2012, pp. 285-313.
Zeitsch, "The Chemistry and Technology of Furfural and its Many By-Products", Sugar Series 13, Elsevier, 2000.
Lange et al., "Furfural—A Promising Platform for Lignocellulosic Biofuels", ChemSusChem, vol. 5, Issue 1, Jan. 9, 2012, pp. 150-166.
Watson. "Butane-1,4-diol from Hydrolytic Reduction of Furan", Ind. Eng. Chem. Prod. Res. Dev., vol. 12, Issue No. 4, Dec. 1973, p. 310.
Pan et al., "Catalytic Conversion of Furfural into a 2,5-Furandicarboxylic Acid-Based Polyester with Total Carbon Utilisation", ChemSusChem, vol. 6, Issue No. 1, Jan. 2013, pp. 47-50.
Dunlop et al., "The Furans", Reinhold Publ. Co., ACS Monograph Series, 1953, 867 pages.

*Primary Examiner* — Taylor V Oh

(57) ABSTRACT

The present invention provides a process for the production of THF and 1,4-BDO from furan in the presence of a catalytic composition, wherein the catalytic composition contains at least one metal selected from the group consisting of Fe, Ru, Os, Co, Rh, Jr, Ni, Pd, Pt and, optionally, contains one or more additional metal on a solid support, and wherein said process comprises the steps of: i) contacting furan with hydrogen and water in a reactor in the presence of said catalytic composition for a time; ii) stopping the flow of furan and the flow of water to the reactor and removing furan and water from the reactor; iii) subjecting the catalytic composition to a gas stream comprising hydrogen at a temperature of from 200 to 600° C. in the absence of the furan and water; iv) re-starting the flow of furan and the flow of water to the reactor.

9 Claims, No Drawings

PROCESS FOR THE PRODUCTION OF 1,4-BUTANEDIOL AND TETRAHYDROFURAN FROM FURAN

PRIORITY CLAIM

The present application is the National Stage (§ 371) of International Application No. PCT/EP2016/057577, filed Apr. 7, 2016, which claims priority from European Patent Application No. 15162903.7, filed Apr. 9, 2015, incorporated herein by reference.

FIELD OF THE INVENTION

The present invention relates a process for the production of 1,4-butanediol and tetrahydrofuran from furan.

BACKGROUND OF THE INVENTION

Furan and its derivatives are useful precursors for industrial chemicals in the area of, for example, pharmaceuticals, herbicides and polymers. Furan may be converted into tetrahydrofuran (THF) and 1,4-butanediol (1,4-BDO). THF and 1,4-BDO are valuable chemicals used industrially as solvents and in the production of elastic fibres such as elastane/spandex, polybutyrate terephthalate and derivatives of gamma butyrolactone.

These chemicals are usually produced industrially via a number of routes from petrochemical feedstocks, obtainable from fossil fuels. In recent years, increased efforts have focused on producing chemicals, including 1,4-BDO and THF, from renewable feedstocks, such as sugar-based materials.

A method for obtaining furan from non-fossil fuel based sources involves the decarbonylation of furfural. Examples of reaction processes for achieving this and the subsequent conversion of the furan into its derivatives can be found in Hoydonck, H E; Van Rhijn, W M; Van Rhijn, W; De Vos, D E; & Jacobs, P A; (2012) Furfural and Derivatives, in Ullmann's Encyclopedia of Industrial Chemistry (volume 16, pp 285-313), Wiley-VCH Verlag GmBH & Co. KGaA, Weinheim; Dunlop, A P; and Peters, F N; in The Furans Reinhold Publ. Co, 1953; K. J. Zeitsch, in "The Chemistry and Technology of Furfural and its Many By products" Sugar Series 13, Elsevier, 2000; Lange, J-P; van der Heide, E; van Buijtenen, J; and Price, R; Furfural—A Promising Platform for Lignocellulosic Biofuels; ChemSusChem 2012, 5, 150-166 and Watson, J. M.; Ind. Eng. Chem. Prod. Res. Develop., 1973, 12(4), 310. Furfural may be obtained from hemicellulose via acid hydrolysis in the liquid phase as well as in the gas phase as described in WO 2002/22593 and WO 2012/041990.

The conversion of furan to THF and 1,4-BDO by hydrogenation in the presence of water, acetic acid and Raney nickel or oxide supported nickel catalyst is described in Watson, J M; Ind. Eng. Chem. Prod. Res. Develop., 1973, 12(4), 310.

A process for the conversion of furan into 1,4-BDO and THF is taught in U.S. Pat. No. 5,905,159. This document teaches a process in which furan is converted as a reaction mixture with water and in the presence of hydrogen but in the absence of a water-soluble acid in a single stage over a hydrogenation catalyst. The hydrogenation catalyst of U.S. Pat. No. 5,905,159 contains at least one element of subgroup I, V, VI, VII or VIII in the form of a compound or in elemental form, with the restriction that the catalyst does not contain nickel alone being applicable. The preferred catalyst in this process is Re/Ru on active carbon. A similar catalyst is used in the process described in Pan, T; Deng, J; Xu, Q; Zuo, Y; Guo, Q-X and Fu, Y; Catalytic Conversion of Furfural into a 2,5-Furandicarboxylic Acid-based Polyester with Total Carbon Utilisation; ChemSusChem 2013, 6, 47-50.

More effective catalysts for the conversion of furan into 1,4-BDO and THF are taught in co-pending applications EP 14196391.8, said catalysts incorporating rhenium and palladium on solid supports and EP 14199023.4, said catalyst incorporating one or more metals from those in group 8, 9, 10 and 11 of the periodic table supported on amorphous or crystalline aluminosilicate supports.

Heterogeneous, supported catalysts of the types finding use in this area have been found to deactivate over time, often due to the presence of carbonaceous deposits (coking). Catalysts that have experiences such deactivation need to be regenerated again. It is known to regenerate by burning off coke from such deactivated catalysts by using a gas stream comprising oxygen, such as an air stream, at an elevated temperature.

Oxidative catalyst regeneration using air is a cumbersome treatment that requires multiple operation steps, dedicated equipment to feed the reactor with either pure $N_2$ (for purge) or air (for coke burn-off). Further, this requires an accurate reactor monitoring for avoiding runaway during the coke burn-off. By applying oxidative catalyst regeneration there is also the hazard connected with a possible mixing of $H_2$ that may be used for the decarbonylation reaction and $O_2$ needed for the regeneration. A further drawback of oxidative catalyst regeneration is that this cannot be applied to catalysts which comprise carbon as a support, because the carbon support would also be burnt under such oxidative conditions.

It is an object of the present invention to provide a process for regenerating a heterogeneous, supported catalyst used in the production of THF and 1,4-BDO from furan, which process does not have the above drawbacks.

SUMMARY OF THE INVENTION

Accordingly, the present invention provides a process for the production of THF and 1,4-BDO from furan in the presence of a catalytic composition, wherein the catalytic composition contains at least one metal selected from the group consisting of Fe, Ru, Os, Co, Rh, Ir, Ni, Pd, Pt and, optionally, contains one or more additional metal on a solid support, and wherein said process comprises the steps of:
i) contacting furan with hydrogen and water in a reactor in the presence of said catalytic composition for a time;
ii) stopping the flow of furan and the flow of water to the reactor and removing furan and water from the reactor;
iii) subjecting the catalytic composition to a gas stream comprising hydrogen at a temperature of from 200 to 600° C. in the absence of the furan and water;
iv) re-starting the flow of furan and the flow of water to the reactor.

DETAILED DESCRIPTION OF THE INVENTION

The present inventors have found that a process for using the production of THF and 1,4-BDO from furan in which a catalytic composition containing at least one metal selected from the group consisting of Fe, Ru, Os, Co, Rh, Ir, Ni, Pd, Pt on a solid support is used, may be improved by carrying out a re-generation step for the catalytic composition in the presence of hydrogen.

It was found that, in contrast with oxidative catalyst regeneration using air, the catalytic composition used in the process of the present invention can be regenerated by applying a relatively simple treatment with hydrogen ($H_2$) at an elevated temperature (200 to 600° C.). This process allows for a simpler and faster regeneration of the catalytic composition, containing fewer process steps, wherein a runaway during coke burn-off cannot take place. Furthermore, because substantially no $O_2$ is used in the present process, there is no hazard connected with a possible mixing of $H_2$ that is used for the furan to THF and 1,4-BDO reaction and $O_2$ needed for the regeneration. Furthermore, in the present invention, no additional equipment is required for the regeneration, in comparison with oxidative regeneration which requires such equipment as dedicated pipelines with valves, flow meters, mixers and controllers to feed air (or air diluted with $N_2$) for regeneration and to accommodate the effluent. In the present invention, neither any additional gas tanks for $N_2$ and air nor air blowers (with purification) are needed. The 'down time' taken up wherein the reactor is not working is also reduced as there is no need for the $N_2$ purges required when replacing hydrogen with oxygen and vice versa. Still further, because substantially no $O_2$ is used in the present regeneration process, the latter process can be applied to catalytic compositions which have (activated) carbon as a support, because the carbon support would not be burned under such non-oxidative conditions.

The catalytic composition used in the process of the present invention contains at least one metal selected from the group consisting of Fe, Ru, Os, Co, Rh, Ir, Ni, Pd, Pt on a solid support. The at least one metal may be present on the catalytic composition in its elemental form or as compounds.

Further to the above-mentioned metal or metals, the catalytic composition used in the present invention may contain one or more additional metals, for example promotor metal or metals that will at least in part catalyse different reactions, such as ring-opening. A suitable example of such an additional metal is rhenium.

The total amount of said metal or metals (considered as elements) including the additional metal or metals, if present on the catalytic composition may vary within wide ranges, and may be of from 0.01 to 20 wt %, 0.1 to 10 wt % or 0.5 to 5 wt % on the basis of the total weight of the catalytic composition. Preferably, the total amount of said metal or metals is at least 0.01 wt %, more preferably at least 0.02 wt %, more preferably at least 0.03 wt %, more preferably at least 0.1 wt %, more preferably at least 0.3 wt %, most preferably at least 1.0 wt %. Further, preferably, the total amount of said metal or metals is at most 20 wt %, more preferably at most 15 wt %, most preferably at most 10 wt %.

The method of application of the metal or metals, including any additional metals, to the support is not critical and may be carried out in a wide range of ways. Suitable methods include, for example, impregnation of the support with solutions or suspensions of the salts, complexes, hydroxides, oxides or other organic or inorganic compounds of the relevant elements, drying and optional calcination. Another possibility for applying the metal or metals to the support is to impregnate the latter with a solution of thermally readily decomposable complexes, for example with carbonyl or hydride complexes of the metal or metals, and to heat the carrier thus impregnated to, for example, 150 to 600° C. for thermal decomposition of the absorbed metal compounds. The at least one metal may furthermore be deposited on the catalytic composition carrier by vapour deposition or by flame spraying. Subsequent reduction of the metal compound(s) to the relevant metal(s) or compounds of lower oxidation states by means of a reducing agent may be carried out after any method of deposition. If more than one metal is used, the metals may be applied to the support using the same or different methods and either sequentially of simultaneously. Preferably, it is more efficient to apply the two or more metals using the same method.

Suitable supports in the present invention include oxides of aluminium, titanium, zirconium, silicon, as such or in combination with other oxides. The support can be amorphous or crystalline, including clays such as montmorillonite or zeolites, such as ZSM-5 or ZSM-10 zeolites. In another embodiment, the support is composed of carbon such as active carbon or carbon fibres. Mixtures of different supports can, of course, also serve as supports for the catalytic compositions to be used in the process of the invention. Preferred supports are titanium oxides, zirconium dioxide and active carbon. More preferred are zirconium dioxide and active carbon. Most preferably, the support is active carbon.

In the process of the invention, the furan is contacted with hydrogen and water in a reactor in the presence of said catalytic composition for a time.

The furan may be contacted with hydrogen and water either in the gas or the liquid phase. Suitable conditions for the production of a mixture of BDO and THF from furan include co-feeding water as a gas or liquid at a water:furan molar ratio in the range of from 0.2:1 to 100:1, preferably in the range of 1:1 to 20:1 and most preferably 3:1 to 10:1. In this embodiment, further suitable conditions include the use of a solvent comprising water and/or oxygenates, preferably the reaction product (THF) or eventually by-products, a temperature in the range of from 100 to 350° C., preferably 120 to 250° C., most preferably 150-200° C., a pressure of from 0.1 to 15 MPa, preferably 1-10 MPa and most preferably 3-7 MPa and a $H_2$:furan molar ratio in the range of from 0.2:1 to 100:1, preferably in the range of from 1:1 to 10:1, most preferably 2:1 to 5:1.

Any suitable reactor may be used for the production of 1,4-BDO and THF from furan. These include, but are not limited to fixed bed and slurry reactors.

The furan is contacted with hydrogen and water in a reactor in the presence of said catalytic composition for a time. Said time will be determined by the individual conditions and can be readily determined by the skilled person. The time is suitably defined such that the catalytic composition will have experienced deactivation by the end of said 'time'. Deactivation of a catalytic composition means that the activity and/or selectivity of said catalytic composition is reduced over time as compared to its original activity (under the same conditions). Said activity may be measured by measuring the conversion of the starting material, or the yield of a product, or the rate constant, under the same conditions (such as temperature). Said selectivity may be measured by measuring the proportion of one or more desirable products formed with respect to the overall yield of all products. Preferably, said selectivity and/or activity for the deactivated catalytic composition is reduced by at most 99.9%, more preferably at most 99%, more preferably at most 90%, more preferably at most 80%, more preferably at most 70%, more preferably at most 60%, more preferably at most 50%, more preferably at most 40%, most preferably at most 30%, as compared to the original activity of said catalytic composition (under the same conditions). Any level of deactivation may require a regeneration step, but preferably, the activity and/or selectivity for said deactivated catalytic composition is reduced by at least 5%, more preferably at least 10% and most preferably at least 20% as compared to the original activity and/or selectivity of said catalytic composition (under the same conditions), before the flow of furan and the flow of water is stopped and the catalytic composition is subjected to a gas stream comprising hydrogen at a temperature of from 200 to 600° C. in the absence of furan and water.

The 'time' for which the furan is contacted with hydrogen and water in the presence of the catalytic composition, is the time it takes for the activity and/or selectivity of the catalytic composition to be reduced by such amounts, i.e. the time it takes for the activity and/or selectivity of the catalytic composition to be reduced by at most 99.9%, more preferably at most 99%, more preferably at most 90%, more preferably at most 80%, more preferably at most 70%, more preferably at most 60%, more preferably at most 50%, more preferably at most 40%, most preferably at most 30% as compared to the original activity and/or selectivity of said catalytic composition (under the same conditions). Preferably, the 'time' is the time it takes for the activity and/or selectivity of the catalytic composition to be reduced by at least 5%, more preferably at least 10%, most preferably at least 20%, as compared to the original activity and/or selectivity of said catalytic composition (under the same conditions).

After said time, the flow of furan and the flow of water to the reactor are stopped. Any remaining furan and water is the reactor is removed from the reactor, for example by draining or purging the reactor.

In the present invention, the catalytic composition is regenerated by subjecting it to a gas stream comprising hydrogen at a temperature of from 150 to 600° C., for example 250 to 450° C., in the absence of the furan and water. Further, preferably, said regeneration temperature is higher than the reaction temperature. Said reaction temperature is the temperature at which the furan was converted to THF and 1,4-BDO before the catalytic composition regeneration step of the present invention is started. More preferably, said regeneration temperature is higher than the initial reaction temperature, which is the reaction temperature at the beginning of the furan to THF and 1,4-BDO reaction step. The latter initial reaction temperature is the lowest reaction temperature in a case wherein the reaction temperature is increased over time during the reaction of furan to THF and 1,4-BDO. Said reaction temperature is not essential and may be of from 100 to 450° C., preferably of from 100 to 350° C., more preferably of from 200 to 350° C., most preferably of from 200 to 300° C. Preferably, said regeneration temperature is at least 10° C. higher, more preferably at least 25° C. higher, more preferably at least 75° C. higher, more preferably at least 100° C. higher and most preferably at least 125° C. higher than the reaction temperature, suitably the initial reaction temperature. Further, preferably, said regeneration temperature is at most 350° C. higher, more preferably at most 300° C. higher, more preferably at most 250° C. higher, more preferably at most 200° C. higher, more preferably at most 150° C. higher and most preferably at most 100° C. higher than the reaction temperature, suitably the initial reaction temperature.

The gas stream that is used in the catalytic composition regeneration step of the present invention and which comprises hydrogen, may comprise one or more additional gases. Said additional gas(es) may be selected from the group consisting of the noble gases, nitrogen ($N_2$), carbon monoxide (CO), carbon dioxide ($CO_2$) and gaseous hydrocarbons such as methane or ethane and steam or mixtures thereof. Preferably, if an additional gas is used, it is $N_2$. A suitable noble gas is argon. Preferably, if one or more additional gases are used, said gas stream comprises hydrogen and the additional gas(es), for example $N_2$, in a volume ratio which is greater than 0.01:1 ($H_2$:additional gas or gases), more preferably greater than 0.1:1, more preferably greater than 1:1, more preferably greater than 5:1, more preferably greater than 10:1, more preferably greater than 50:1, more preferably greater than 100:1 and even more preferably greater than 1000:1. Most preferably, the gas stream used in the catalytic composition regeneration process of the present invention consists of hydrogen, which means that it contains substantially no gases other than the hydrogen gas. For example, in the latter embodiment, the amount of hydrogen in said gas stream may be greater than 99 vol %, suitably greater than 99.9 vol %, more suitably greater than 99.99 vol %.

Preferably, the flow of $H_2$ (per gram of catalytic composition and per hour) used during the catalytic composition regeneration steps of the present invention is greater than the flow of $H_2$ (per gram of catalytic composition and per hour) used during the previous step for the conversion of furan to THF and 1,4-BDO.

Substantially no oxygen is used in the regeneration process. Unlike in prior art processes, the catalytic composition is not heated in the presence of oxygen before treatment with the gas stream comprising hydrogen.

Preferably, in view of the presence of $H_2$, no $O_2$ is present in the gas stream comprising hydrogen used in the catalytic composition regeneration step of the present invention. If, however, some $O_2$ is present in said gas stream, the amount thereof is suitably smaller than 1 vol %, suitably smaller than 0.01 vol %, more suitably smaller than 0.001 vol %, most suitably smaller than 0.0001 vol %.

The pressure of the gas stream comprising hydrogen used in the catalytic composition regeneration step of the present invention may be in the range of from 0.1 to 20 MPa, suitably 0.2 to 10 MPa, more suitably 0.3 to 5 MPa and most suitably 0.5 to 1.5 MPa. Further, the hydrogen gas may be fed at a rate of 0.01 to 100 Nl/g/h (normal liter per gram of catalytic composition per hour), preferably 0.1 to 50 Nl/g/h, more preferably 1 to 10 Nl/g/h.

After the regeneration step of the process of the present invention, the flow of furan and water to the reactor is re-started. Prior to re-starting the flow, the reactor may be cooled or allowed to cool to a lower temperature than used in the regeneration step.

The reaction of furan to THF and 1,4-BDO may then be continued under suitable conditions.

The process of the present invention may be repeated, as necessary, with any number of regeneration steps being interspersed between reaction steps.

The invention will now be illustrated by the following non-limiting examples.

Examples

Catalysts were evaluated in a four-barrel microflow unit that consists of 4 parallel Hastelloy HC 276 reactor (1 cm ID). The reactors had an isothermal zone of 25 cm length and an internal volume of 41 mL. The reactors can be operated between 40 and 500° C. under 1.5 to 140 bar pressure. The liquid feed was fed to the reactor by 1000 mL ISCO 1000D pumps with a maximum flow rate of 100 mL/h.

Hydrogen was applied to the reactor through a mass flow controller with a maximum flow rate of 5 NL/h.

The catalysts were loaded as crushed (30-80 mesh) particles, as 3 g load, and diluted in an equal weight of SiC (0.2 mm). The catalysts in each reactor consisted of an active carbon (RX3, commercially available from Norrit) that was impregnated with 4 w % of Re and 0.04 w % of Pd.

The initial catalyst reduction was carried at 275° C. for 16 h under atmospheric pressure and 1 Nl/h flow of 50 vol % $H_2$ in $N_2$ and, subsequently, for 2 h at 4 bara and a 1 NL/h flow of pure 100% $H_2$. After reduction the temperature was lowered to 200° C., the $H_2$ flow and pressure were set to target and the furan-containing liquid flow was admitted to the reactor.

The reaction was then carried out over a wide operation window for some 900 h. The window covered temperatures of 130-200° C., pressures of 30-130 bar, WHSV of 0.2-2/h, and feed concentrations of 12-30 w % for furan and 27-34 w % for water with EtOH as balance. However, the catalyst was regularly run under reference conditions to quantify the catalyst deactivation, the results of which are shown in Table 1. This reference condition consisted of 150° C. and 50 bar with a liquid feed consisting of 23 w % furan, 30 w % water and 47 w % EtOH and fed at a WHSV of 2 g/g/h and a constant H2/furan molar ratio of 2.5.

After some 900 h on stream, the catalyst was subjected to a regeneration step that consists of stopping the liquid feed, draining the reactor for 30 min, raising the reactor temperature to 400° C. within 10 h, maintaining it at 400° C. for 4 h, cooling back to 150° C. within 16 hours and resuming the liquid feed under reference conditions.

Table 1 reports the furan conversion and the yield of THF, BDO, NBA and GBL measured under reference conditions over the time on stream. It clearly illustrates the slow deactivation of the catalyst and its successful regeneration upon treatment under $H_2$ at 400° C.

TABLE 1

| Time h | Conversion % | THF Yield % | BDO Yield % | NBA Yield % | GBL Yield % |
|---|---|---|---|---|---|
| 216 | 95.6 | 67 | 31 | 5 | 2 |
| 378 | 77.1 | 45 | 32 | 4 | 2 |
| 528 | 66.4 | 43 | 28 | 4 | 2 |
| 661 | 65.3 | 42 | 25 | 4 | 2 |
| 865 | 65.0 | 39 | 23 | 4 | 1 |
| Regeneration at 400° C. | | | | | |
| 917 | 98.1 | 67 | 35 | 5 | 2 |

That which is claimed is:

1. A process for the production of tetrahydrofuran and 1,4-butanediol from furan in the presence of a catalytic composition, wherein the catalytic composition contains at least one metal selected from the group consisting of Fe, Ru, Os, Co, Rh, Ir, Ni, Pd, Pt and, optionally, contains one or more additional metal on a solid support, and wherein said process comprises the steps of:
    i) contacting furan with hydrogen and water in a reactor in the presence of said catalytic composition for a time;
    ii) stopping the flow of furan and the flow of water to the reactor and removing furan and water from the reactor;
    iii) regenerating the catalytic composition by subjecting the catalytic composition to a gas stream comprising hydrogen at a temperature of from 200 to 600° C. in the absence of the furan and water;
    iv) re-starting the flow of furan and the flow of water to the reactor.

2. The process according to claim 1, wherein the catalyst contains one or more additional metals, comprising rhenium.

3. The process according to claim 1, wherein in step i) the furan is contacted with hydrogen and water in a reactor in the presence of said catalytic composition for the time it takes for the activity of the catalytic composition to be reduced by at least 5% and at most 90%, as compared to the original activity of said catalytic composition under the same conditions.

4. The process according to claim 1, wherein the temperature at which the catalytic composition is subjected to a gas stream comprising hydrogen in step iii) is at least 25° C. higher than the temperature at which furan is contacted with hydrogen and water in a reactor in the presence of said catalytic composition for a time.

5. The process according to claim 1, wherein the temperature at which furan is contacted with hydrogen and water in a reactor in the presence of said catalytic composition for a time is in the range of from 100 to 350° C.

6. The process according to claim 5, wherein the temperature at which the catalytic composition is subjected to a gas stream comprising hydrogen in step iii) is in the range of from 250 to 450° C.

7. The process according to claim 1, wherein the solid support is selected from the group consisting of titanium oxides, zirconium oxides and active carbon.

8. The process according to claim 1, wherein the reactor is cooled prior to re-starting the flow of furan and the flow of water to the reactor.

9. The process according to claim 1, wherein the process of steps i) to iv) are repeated more than once with the same catalytic composition.

* * * * *